United States Patent [19]
Tam

[11] Patent Number: 5,578,569
[45] Date of Patent: Nov. 26, 1996

[54] METHOD OF INCREASING BONE GROWTH

[76] Inventor: Cherk S. Tam, 1072 Rectory Lane, Oakville, Ontario L6M 2B7, Canada

[21] Appl. No.: 229,009

[22] Filed: Apr. 18, 1994

Related U.S. Application Data

[63] Continuation-in-part of Ser. No. 120,217, Sep. 13, 1993, abandoned, which is a continuation-in-part of Ser. No. 31,386, Mar. 12, 1993, abandoned.

[51] Int. Cl.$^6$ ................................................ A61K 38/18
[52] U.S. Cl. .......................... 514/12; 530/300; 530/399
[58] Field of Search ............................ 514/12; 530/300, 530/399

[56] References Cited

U.S. PATENT DOCUMENTS

| | | | |
|---|---|---|---|
| 4,897,348 | 1/1990 | Johnson et al. | 435/69.1 |
| 5,024,841 | 6/1991 | Chu et al. | 424/422 |
| 5,264,214 | 11/1993 | Rhee et al. | 424/422 |
| 5,470,911 | 11/1995 | Rhee et al. | 530/402 |

FOREIGN PATENT DOCUMENTS

| | | |
|---|---|---|
| 2231872 | 7/1992 | United Kingdom . |
| WOA9000060 | 1/1990 | WIPO . |
| WO90/06321 | 6/1990 | WIPO . |
| 9111515 | 8/1991 | WIPO . |
| WO94/05309 | 3/1994 | WIPO . |

OTHER PUBLICATIONS

Begg et al "Complete Covalent Structure of Human β–Thromboglobulin" *Biochem* 17(9):1739–1744.
Castor et al. Connective Tissue Activation, Arthritis & Rheumatism, vol. 35, No. 7 (Jul. 1992) pp. 783–793.
Castor et al. Structural and Biological Characteristics of Connective Tissue Activating peptide (CTAP–III), a Major Human Plaelet–Deived Growth Factor, Proc. Natl. Acad. Sci. USA, vol. 80, pp. 765–769 (Feb. 1983).
Tam, "The Pathogenesis of Metabolic Bone Disease . . . " CRC Press, Boca Raton 2: 19–31 (1989).
Parfitt, "The Coupling of Bone Formation to Bone . . . " Metab. Bone Dis. & Rel. Res. 4:1–6 (1982).
Coccia et al. "Successful Bone–Marrow Transplantation . . . " New Eng. J. Med. 302(13) 701–708 (1980).
Marks et al., "The Hematogenous Origin of Osteoclasts: Experimental . . . " Am. J. Anat 161: 1–10 (1981).
Owen, "Lineage of Osteogenic Cells and Their . . . " Bone & Mineral Res. 3(1):1–25 (1985).
Canalis, "Interleukin–1 Has Independent Effects on Deoxyribonucleic . . . " Endocrinology 118(1):74–81 (1986).
Centrella et al., "Transforming and Nontransforming Growth Factors Are . . . " Proc. Natl. Acad. Sci. USA 82: 7335–7339 (Nov. 1985).
Canalis, "Effect of Growth Factors on Bone Cell . . . " Clin. Orthop. & Rel. Res. 246–263 (1985).
Chyun, "Stimulation of Bone Formation by Prostaglandin E2" Prostaglandins J. 27(1): 97–103 (Jan. 1984).
Canalis, "Effect of Insulinlike Growth Factor I on DNA . . . " J. Clin. Invest. 66: 709–719 (Oct. 1980).
Klein et al., "Prostaglandins: Simulation of Bone Resorption . . . " Endocrinology 86: 1436–14 1440 (Jun. 1970).
Tashjian et al. "α and β Human Transforming Growth Factors . . . " Proc. Natl. Acad. Sci. USA 82: 4535–4538 (Jul. 1985).
Chen, "Glucocorticoid Regulation of 1.25(OH)2–Vitamin D3 . . . " J. Bio. Chem. 257(22): 13564–13569 (Nov. 1982).
Roodman, "Perspectives: Interleukin–6: An Osteotropic Factor?" J. Bone & Mineral Res. 7(5): 475–478 (1992).
Selye, "On the Stimulation of New Bone–Formation . . . " Endocrinology 16: 547–558 (1933).
Aitken et al. "Primary Hyperparathyroidism with Osteosclerosis . . . " Am. J. Med. 37: 813–820 (Nov. 1964).
Connor et al., "Generalized Osteosclerosis in Primary . . . " Trans Am. Clin. Climato. Assoc. 85: 185–201 (1973).
Genant, "Osteosclerosis in Primary Hyperparathyroidism" Am. J. Med. 59: 104–113 (Jul. 1975).
Kalu et al., "Parathyroid Hormone and Experimental . . . " Lancet 1363–1366 (Jun. 1970).
Tam et al., "Bone Apposition Rate as an Index of . . . " Metabolism 27(2): 143–150 (Feb. 1978).
Tam et al., "Bone Biopsy in the Diagnosis of Primary . . . " Endoc. Calc. Metab. Excerpa Med. 427 (Abstract).
Majumdar et al. "Characterization of the Human β–Thromboglobulin . . . " J. Bio. Chem. 266(9): 5785–5787 (Mar. 1991).
Tam et al., "Parathyroid Hormone Stimulates the Bone . . . " Endocrinology 110(2): 506–512 (1982).
Brandt et al, "Characterization of a Platelet Derived Factor . . . " Lymphokine Res. 8(3): 281–287.
Castor et al, "Connective Tissue Activation . . . " Biochem. Biophys. Res. Comm. 163(2):1071–1078 (Sep. 1989).
Walz et al, "Generation of the Neutrophil–Activating Peptide NAP–2 . . . " J. Exp. Med. 171:449–454 (Feb. 1990).

*Primary Examiner*—Stephen G. Walsh
*Attorney, Agent, or Firm*—Foley & Lardner

[57] ABSTRACT

A polypeptide isolated from human blood serum has been found to increase bone growth in rats. The peptide is thought to have the seventy-five amino acid sequence of a previously sequenced variant of NAP-2V: Asp Ser Asp Leu Tyr Ala Glu Leu Arg Cys Met Cys Ile Lys Thr Thr Ser Gly Ile His Pro Lys Asn Ile Gln Ser Leu Glu Val Ile Gly Lys Gly Thr His Cys Asn Gln Val Glu Val Ile Ala Thr Leu Lys Asp Gly Arg Lys Ile Cys Leu Asp Pro Asp Ala Pro Arg Ile Lys Lys Ile Val Gln Lys Lys Leu Ala Gly Asp Glu Ser Ala Asp (SEQ ID NO:4).

12 Claims, 6 Drawing Sheets

METHOD OF INCREASING BONE GROWTH

This is a continuation in-part of application Ser. No. 120,217 filed Sep. 13, 1993 (now abandoned) which is a continuation-in-part of application Ser. No. 031,386 filed Mar. 12, 1993, now abandoned. The specifications of both of these prior applications are incorporated herein by reference.

It is known that even in the adult human, bone is subject to turnover. In certain locations, such as the internal auditory capsule, there is apparently no turnover after the organ is formed. In other locations, particularly in the central skeletal axis, the turnover appears to continue during adulthood. Bone turnover occurs on the surface of the existing bone matrix, which is composed of protein (mainly collagen) and minerals. Bone turnover is initiated with the destruction of bone matrix by osteoclasts. The osteoclast is a multinucleated cell which secretes acid and proteolytic enzymes leading to the lysis of the collagen matrix protein and the release of minerals into the extracellular fluid compartment. Following this initial phase of bone destruction, or resorptive phase, formation of new bone protein matrix sets in. New bone proteins are deposited, and sometime later, minerals begin to be incorporated into the newly formed matrix. The formation of bone matrix and its subsequent mineralization are functions of osteoblasts, which are mononucleated cells. The formation phase is often followed by a period of inactivity (1,2). In vivo, resorption appears to be tightly coupled with formation (3) and bone turnover is thus a succession of events, the location of which is known as the Bone Metabolism Unit or the BMU. Osteoblasts and osteoclasts, the putative mediators of bone turnover are thought to belong to two distinct cell lineages. These two cell types are not preformed cells, but they differentiate from their precursors through cell activation (4,5,6).

Bone matrix can either be maintained by a cessation of bone turnover as for the bone of the internal auditory capsule, or by a balance between resorption and formation. In many studies on skeletal changes in relation to age, a gain in the total body bone volume is observed during the growth period and the skeletal mass reaches a maximum during early adulthood. This gain is followed by a fall in bone volume with age. In females, a phase of more rapid bone loss often occurs during the perimenopausal period before a slower steadier phase. For this reason, bone loss in the female tends to be more severe than in the male. An understanding of bone balance in the BMU may thus be critical to understanding the pathogenesis of skeletal aging. In any case, mechanisms controlling bone turnover are complex and are not well understood at this time. The complexity of the control mechanisms has resulted in a variety of approaches to reducing bone loss.

Bone turnover can be regulated at two different stages. It can be regulated at the stage of the activation of precursor cells. Regulators of cellular activation can control not only the number of active BMU in the skeleton, but possibly also the number of osteoclasts and osteoblasts in an individual BMU. Bone turnover secondly can be regulated at the level of differentiated bone cells. The complexity of the bone cell system makes the separate study of these two levels of regulation difficult (3).

Regulators of bone cells appear to fall into two categories. The first type interacts with specific receptors on cell membranes. One class of these regulators acts through the adenylate cyclase system with the generation of intra-cellular cyclic AMP as the second messenger acting on the protein kinase K system. Parathyroid hormone (PTH) and calcitonin (CT) belong to this class (7). A second class also interacts with a membrane receptor and results in the intracellular release of a molecule derived from phosphoinositides which in turn leads to an increase in intracellular calcium and activation of Kinase C. A third class involves interaction of the regulator with a cell surface receptor, but the second signal is generated by the receptor molecule itself with the subsequent activation of tyrosine Kinase. Many of the growth factors appear to act in this way (8–15). Regulators falling into the second category do not interact with a cell membrane receptor, but can cross the cell membrane to bind with a cytosolic receptor. The regulator is then transported across the nuclear membrane by the cyctosolic receptor to interact with the DNA resulting in increased transcription of specific genes. Steroid hormones, including vitamin D, appear to act in this manner (16).

Many hormones stimulate the proliferation of osteoclasts. These include $1,25(OH)_2D$, PTH and prostaglandins. PTH and $1,25(OH)_2D$ receptors in osteoclasts have apparently not yet been identified. These two hormones seem to have no effect on osteoclasts in culture. However, when osteoclasts are co-cultured with osteoblast-like cell lines, PTH and $1,25(OH)_2D$ stimulate the proliferation of osteoclasts. IL-1 and TNF appear to act in a similar way as PTH and $1,25(OH)_2D$. Other growth factors, like EGF, TFG and PDGF appear to stimulate osteoclasts through increased production of PGE. Calcitonin and corticosteroids are known osteoclast inhibitors along with chemicals such as diphosphonates.

It is currently believed that interleukin 1 may stimulate collagen and non-collagen bone protein and DNA synthesis. The effect on bone protein synthesis is blocked by indomethacin, suggesting that this action of IL-1 is mediated through PGE. Indomethacin seems to have no effect on the IL-1 effect on osteoblast DNA synthesis. In culture studies on osteoblast-like cell lines suggest that some locally produced growth factors stimulate DNA and collagen synthesis. In bone cell culture, PTH or Vitamin D suppresses collagen synthesis. This in vitro effect of PTH contrasts with the in vivo effect observed in human subjects and experimental animals. It has been demonstrated in rats and in human hyperparathyroid patients that PTH can stimulate the deposition of mineralized bone matrix. Preliminary clinical trial studies on the efficacy of the PTH 1–34 amino acid fragment in the treatment of osteoporosis indicate that this PTH fragment can increase the trabecular volume. The reason for this discrepancy is not yet fully explained.

Parathyroid hormone is a peptide of 84 amino acids in its mature form. Initially translated pre-pro-parathyroid hormone is much larger, the pre sequence being a signal sequence which is cleaved when the peptide enters the rough endoplasmic reticulum. In the golgi apparatus, the pro-sequence is cleaved off leaving the intact mature hormone packaged in the secretory granule. It appears that regulation of the rate of secretion is governed not so much by the rate of production of the intracellular peptide, but in the rate of intracellular destruction and in the rate of secretion. Intracellularly, the mature peptide is truncated at both the amino and the carboxyl termini. The truncated peptide may be secreted into circulation as an inactive fragment. The secretion of the mature peptide can be stimulated by a drop in the extracellular calcium concentration. An elevated serum calcium concentration on the other hand appears to suppress the secretion of PTH. Once in circulation, the mature peptide is rapidly cleaved in the liver at many sites of the molecule including the region of the 38 amino acid residue. The smaller fragment at the amino terminal end, which includes the first 34 amino acids, carries the full known biological activity in terms of its action on the kidney, the intestine and the bone. It also binds fully to the cell membrane receptor to stimulate cAMP production. The level of the 1–38 fragment in the serum is normally unmeasurable indicating that it has a short circulatory life. The larger inactive carboxyl terminal fragment has a relatively long half life and carries the highest proportion of the immunoreactive PTH in the circulatory system. All fragments in circulation are eventually destroyed in the kidney and the liver. One of the renal mechanisms for elimination of the circulating inactive PTH fragments is glomerular filtration (17).

PTH participates in calcium and skeletal homeostasis. PTH stimulates the tubular resorption of calcium by the kidney and inhibits the reabsorption of phosphate and bicarbonate by the proximal renal tubules. A second effect of PTH on the kidney is the stimulation of 1,25(OH)$_2$D production. This vitamin D metabolite is an in vivo stimulator of osteoclasts as well as an enhancer of intestinal calcium absorption. The increase in calcium absorption by the intestine following PTH stimulation is mediated by this vitamin D metabolite. In vivo, PTH stimulates osteoclastic bone resorption with the release of calcium into the circulation. PTH also causes proliferation of osteoblasts (18). In many cases of hyperparathyroidism there is a skeletal loss. However, an increase in spinal density has been reported in some cases of primary hyperparathyroidism (19,20,21) as well as in secondary hyperparathyroidism complicating renal failure. Kalu and Walker have observed that chronic administration of low doses of parathyroid extract led to sclerosis of bone in the rat (22). Tam et al. studied the effect of low calcium diet on the bone mineral apposition rate in the rat by tetracycline labelling and found that despite the loss of bone due to increase in bone resorption histologically (as a result of secondary hyperparathyroidism), the bone mineral apposition rate was increased (23). It was also found that the bone mineral apposition rate was increased in 23 human patients with mild primary hyperparathyroidism (24). After successful removal of parathyroid adenoma from four of the patients, the rate returned to the level observed in control subjects. There has also been found to be a dose dependent stimulation of the mineral apposition rate by PTH. The potency of the 1–34 fragment and the intact PTH hormone appears to be about the same on a molar basis. This is consistent with the 1–34 fragment of the PTH molecule carrying the biological activity of the intact hormone. It has also been observed that the end result of the administration of PTH on skeletal homeostasis depends on how the hormone is administered. For the same daily dose, the bone volume shows a dose dependent increase if the daily dose of the hormone is given as one single injection. However, when the same daily dose is administered by continuous infusion with a subcutaneous miniosmotic pump, the result is bone loss. Intermittent injection causes practically no effect on the serum calcium levels whereas infusion causes a dose dependent increase in the serum calcium. The effects of PTH administered by these two routes on bone mineral apposition rate as measured by tetracycline labelling are the same. What accounts for this differential effect is not understood (25).

Given the general understanding of bone growth and its regulation, various approaches to treatment of diseases involving reduction of bone mass and accompanying disorders are exemplified in the patent literature. For example, PCT Patent Application No. 9215615 published Sep. 17, 1992 describes a protein derived from a porcine pancreas which acts to depress serum calcium levels for treatment of bone disorders that cause elevation of serum calcium levels. European Patent Application No. 504938 published Sep. 23, 1992 describes the use of di- or tripeptides which inhibit cysteine protease in the treatment of bone diseases. PCT Patent Application No. 9214481 published Sep. 3, 1992 discloses a composition for inducing bone growth, the composition containing activin and bone morphogenic protein. European Patent Application No. 499242 published Aug. 19, 1992 describes the use of cell growth factor compositions thought to be useful in bone diseases involving bone mass reduction because they cause osteoblast proliferation. PCT Patent Application No. 4039656 published Jun. 17, 1992 describes a drug containing the human N-terminal PTH fragment 1–37. European Patent Application No. 451867 published Sep. 16, 1991 describes parathyroid hormone peptide antagonists for treating dysbolism associated with calcium or phosphoric acid, such as osteoporosis.

The relatively short half life of PTH in the blood serum and the relatively lengthy effect of intermittent PTH injection led the present investigator to the hypothesis that PTH may in some way lead to induction of a second factor into the circulatory system. The presence of such a second factor in blood serum of rats and of humans has thus been investigated.

As disclosed in prior application Ser. Nos. 031,386 (now abandoned) and 120,217 (now abandoned) naming as the inventor the sole inventor named in this application, it has been found possible to isolate from rat blood serum a polypeptide substance which, upon administration to rats incapable of producing PTH (parathyroidectomized rats), produces an increase in the observed bone mineral apposition rate as determined using tetracyline labelling.

Further, as disclosed in the earlier applications, a nucleic acid probe, based on the amino acid sequence of the rat polypeptide has been synthesized and used to screen a human liver cDNA fetal library in order to isolate a human nucleic acid sequence coding for a human bone apposition polypeptide. A chemically synthesized polypeptide corresponding to a portion of the isolated sequence was found to increase the bone apposition rate in rats in a dose dependent fashion as determined using tetracyline labelling.

It has also been possible to isolate a polypeptide from human blood serum capable of causing an increased bone mineral apposition rate in parathyroidectomized rats.

The first eighteen amino acids of the N-terminus of the human isolate, termed here "human bone stimulating factor" have now been determined to be resemble a sequence contained in certain previously isolated polypeptides: human β-thromboglobulin (βTG), connective tissue-activating peptide III (CTAP-III) and a variant of neutrophil-activating peptide (NAP-2).

The sequence of βTG was published by Poncz et al. in 1991 (26): Gly Lys Glu Glu Ser Leu Asp Ser Asp Leu Tyr Ala Glu Leu Arg Cys Met Cys Ile Lys Thr Thr Ser Gly Ile His Pro Lys Asn Ile Gln Ser Leu Glu Val Ile Gly Lys Gly Thr His Cys Asn Gln Val Glu Val Ile Ala Thr Leu Lys Asp Gly Arg Lys Ile Cys Leu Asp Pro Asp Ala Pro Arg Ile Lys Lys Ile Val Gln Lys Lys Leu Ala Gly Asp Glu Ser Ala Asp (SEQ ID NO:1).

Walz et al. has published polypeptide sequences identified as neutrophil-activating peptide (NAP-2)(27): Ala Glu Leu Arg Cys Met Cys Ile Lys Thr Thr Ser Gly Ile His Pro Lys Asn Ile Gln Ser Leu Glu Val Ile Gly Lys Gly Thr His Cys Asn Gln Val Glu Val Ile Ala Thr Leu Lys Asp Gly Arg Lys Ile Cys Leu Asp Pro Asp Ala Pro Arg Ile Lys Lys Ile Val Gln Lys Lys Leu Ala Gly Asp Glu Ser Ala Asp (SEQ ID NO:2); and CTAP-III, (27): Asn Leu Ala Lys Gly Lys Glu Glu Ser Leu Asp Ser Asp Leu Tyr Ala Glu Leu Arg Cys Met Cys Ile Lys Thr Thr Ser Gly Ile His Pro Lys Asn Ile Gln Ser Leu Glu Val Ile Gly Lys Gly Thr His Cys Asn Gln Val Glu Val Ile Ala Thr Leu Lys Asp Gly Arg Lys Ile Cys Leu Asp Pro Asp Ala Pro Arg Ile Lys Lys Ile Val Gln Lys Lys Leu Ala Gly Asp Glu Ser Ala Asp (SEQ ID NO:3). These sequences have also been described in PCT Patent Application No. 9006321 published Jun. 14, 1990.

Walz et al. also identified a variant of NAP-2 as a cleavage product of the platelet α-granule component platelet basic protein (PBP), which is termed here NAP-2V (27): Asp Ser Asp Leu Tyr Ala Glu Leu Arg Cys Met Cys Ile Lys Thr Thr Ser Gly Ile His Pro Lys Asn Ile Gln Ser Leu Glu Val Ile Gly Lys Gly Thr His Cys Asn Gln Val Glu Val Ile Ala Thr Leu Lys Asp Gly Arg Lys Ile Cys Leu Asp Pro Asp Ala Pro Arg Ile Lys Lys Ile Val Gln Lys Lys Leu Ala Gly Asp Glu Ser Ala Asp (SEQ ID NO:4). NAP-2V is related to NAP-2 in that NAP-2V has an additional five amino acid residues located at its N-terminus and the N-terminus of NAP-2V resembles the N-terminus of the first twenty amino acids of the human bone stimulating factor.

The results of Walz et al. suggest that NAP-2V is not an obligatory intermediate of NAP-2 formation (27 at page 453). While Walz et al. also found that NAP-2V had considerably less neutrophil-stimulating activity than NAP-2, the precise function of either NAP-2 or NAP-2V remains unknown.

DESCRIPTION OF THE DRAWINGS

In the following description, reference is made to accompanying drawings, wherein.

RESULTS INVOLVING NATURALLY OCCURRING HUMAN BONE STIMULATING FACTOR

Figure 1:
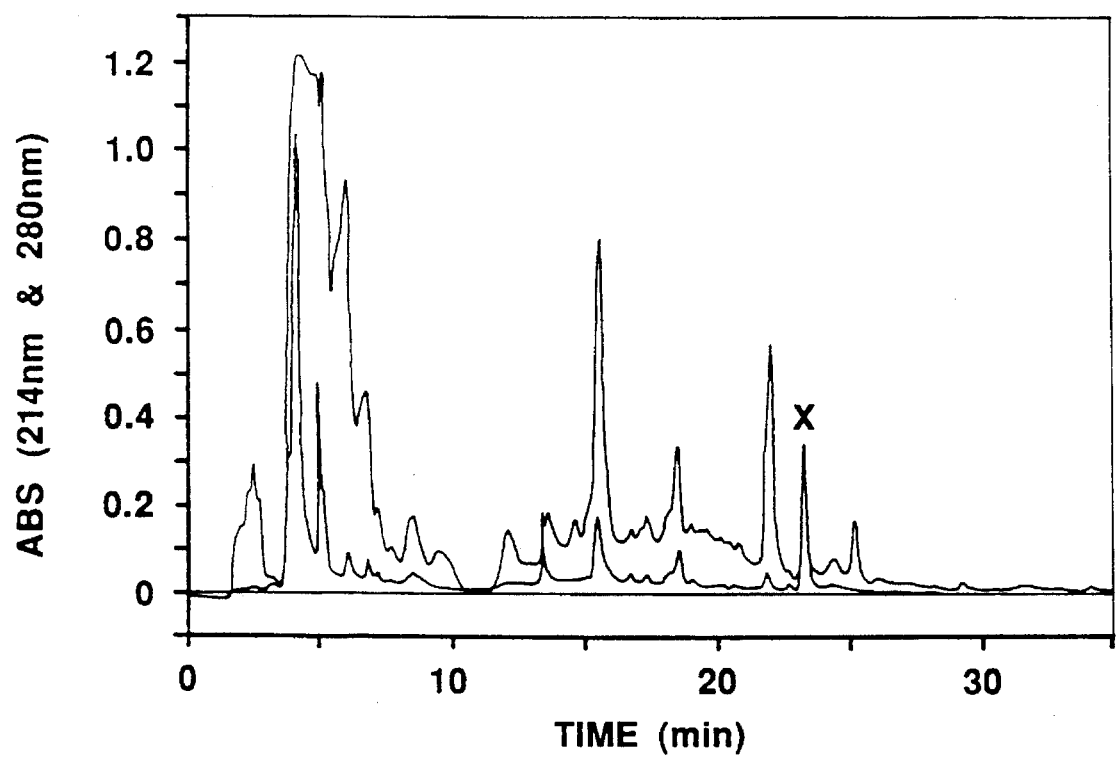
FIGS. 1 to 3 are reverse phase HPLC chromatograms of human serum fraction with molecular weight between 30K and 3K. A 36.4 ml volume of human serum pooled from patients with renal failure was used. The serum was subjected to ultrafiltration to collect a fraction with MW between 30K-3K. This fraction was concentrated to about 2 ml and loaded 3 times onto a Beckman C8 column (4.6 mm×150 mm) and run in a gradient of 10 mM Tris.Cl (pH 7.2) and 10% $CH_3CN$. There was a peak obtained at about 20% $CH_3CN$. Peaks from all three runs were collected and pooled. The uppermost scans were taken at 214 nm.
Figure 2:
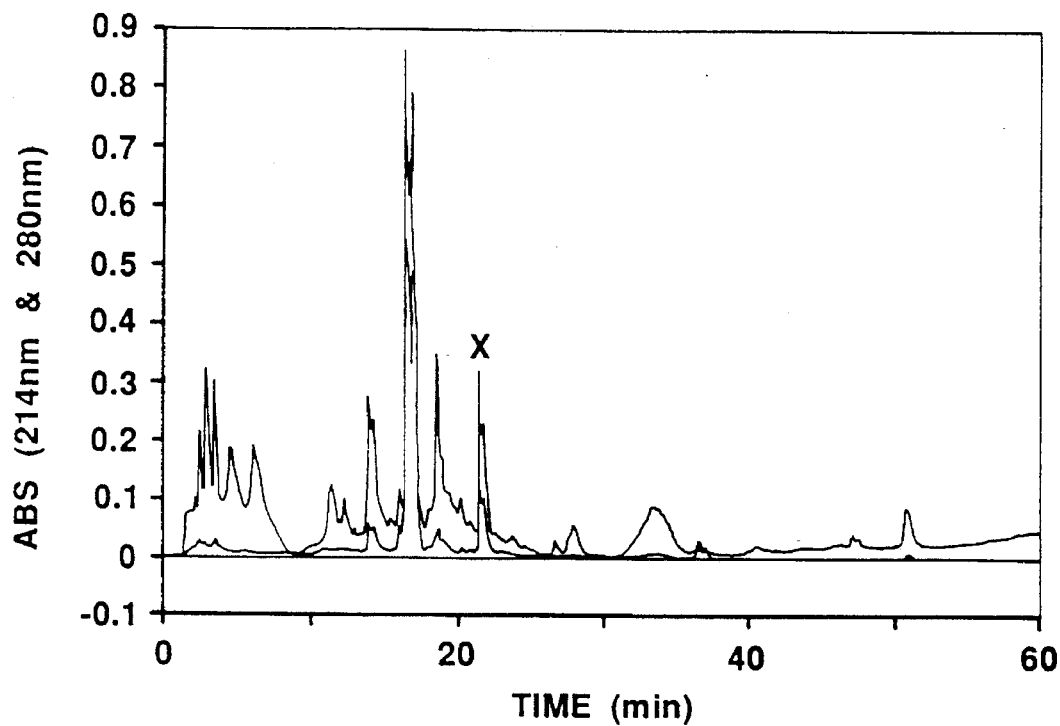
Figure 3:
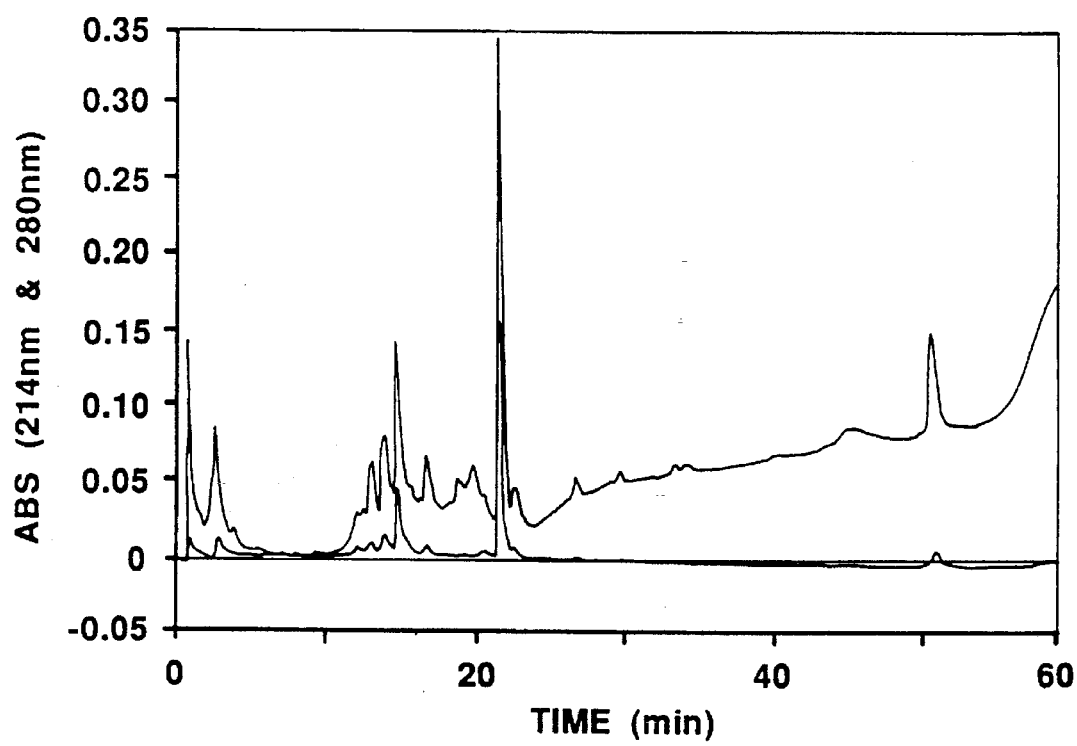
Figure 4:
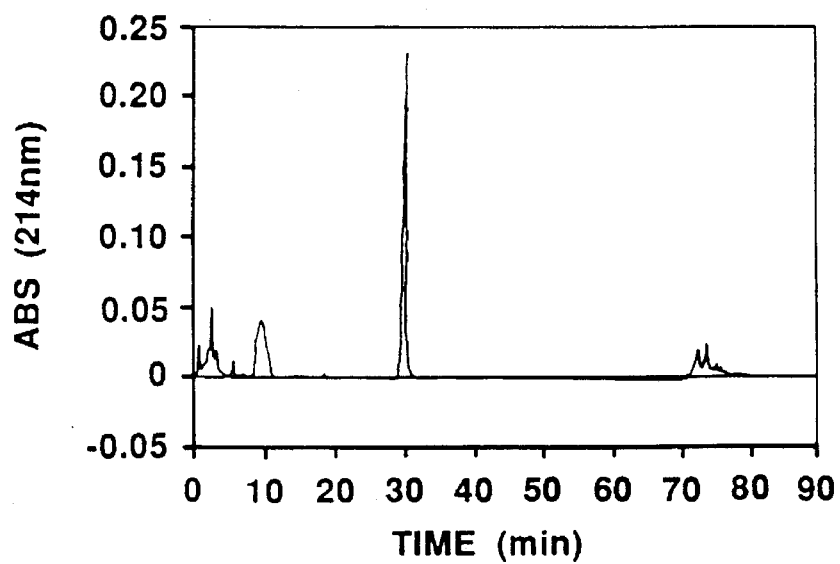
FIG. 4 is a chromatogram showing further purification of a human serum fraction by C3 reverse phase HPLC. The pooled "x" peaks from FIGS. 1 to 3 were lyophilized and redissolved in 20 mM Tris.Cl (pH 7.2) and run on a Beckman C3 column (4.6 mm×75 mm). The gradient condition was the same. A single resolved peak eluted at 30 min (about 25 % $CH_3CN$). This peak was collected.
Figure 5:
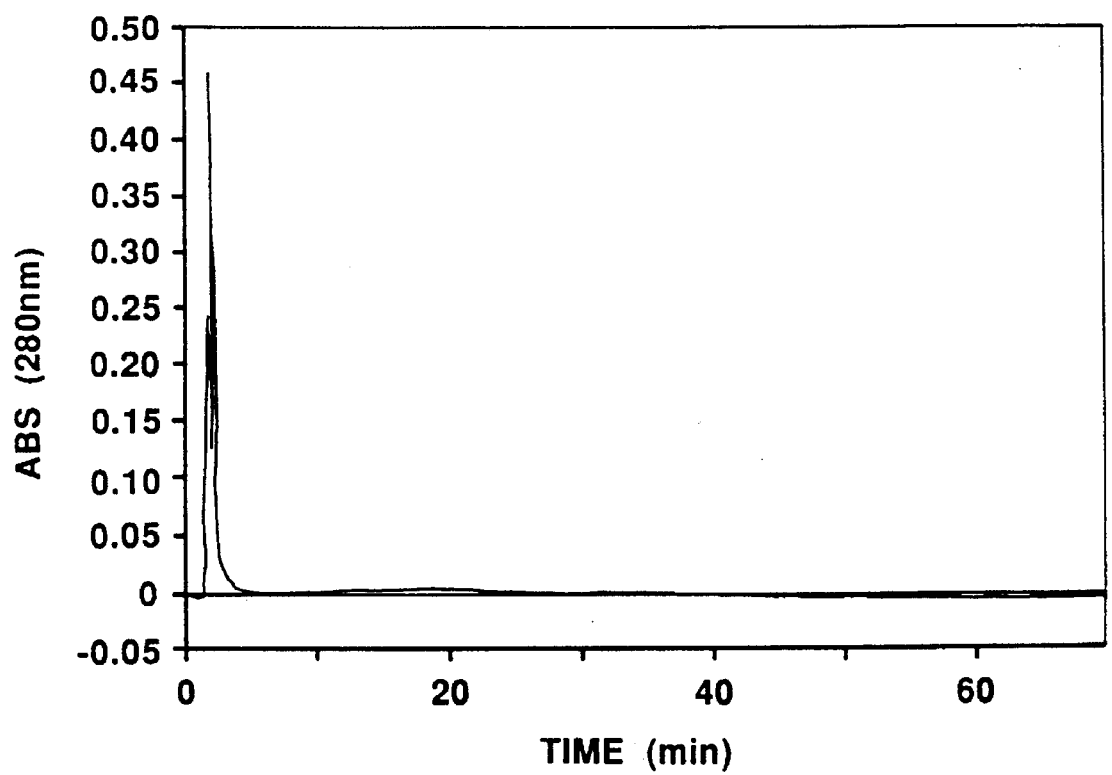
FIG. 5 shows a C8 reverse phase HPLC chromatogram of a serum fraction with MW between 30K and 3K from a normal subject. The whole serum was treated as before to collect the fraction with 30 to 3K MW. The C8 reverse phase chromatography was performed under the same conditions as stated in FIGS. 1 to 3. No material was retained by the column from the serum of the normal subject.

INITIAL RESULTS INVOLVING A BONE STIMULATING FACTOR IN THE LOW MOLECULAR WEIGHT FRACTION OF HUMAN SERUM FROM PATIENTS WITH RENAL INSUFFICIENCY

As discussed above, human patients with renal failure may show increase in bone density in the radiological examination of the skeleton. These patients, because of an impaired renal synthesis of 1,25 dihydroxyvitamin D, have impaired intestinal calcium absorption and often suffer secondary hyperparathyroidism. Further, glomerular filtration of such patients may be reduced because of a reduction in the number of normal glomeruli. Many low molecular weight peptides may accumulate at higher than normal concentrations because of impaired glomerular filtration.

Human serum was collected from patients of the Queen Elizabeth Hospital of Toronto, Ontario, Canada suffering from mild to moderately severe renal insufficiency. Samples were remains of blood taken for clinical biochemical tests. Blood urea nitrogen was over 7 mM. Some serum samples were also from patients with severe renal insufficiency periodically attending a hemodialysis clinic in the Western Division of the Toronto Hospital Corporation, Toronto. A total of 36.4 ml of serum was collected.

Human control serum was obtained from 80 ml of blood taken 40 ml at a time from a normal human subject. After centrifugation 37.5 ml of serum were obtained and 36.4 ml was taken for fractionation. The pooled serum was centrifuged in a Beckman J2-21 centrifuge at 12,000 g for 30 minutes at 4° C., using a JA 17 rotor. PMSF (phenylmethane sulfonyl fluoride) and DTT (dithiothreitol) were added to give a concentration of 1 mM each.

Serum components of molecular weights between 3,000 and 30,000 were fractionated by ultrafiltration, according to the method described in connection with rat serum in U.S. patent application Ser. No. 08/120,217. The final volume each of the test and control samples was 2 ml and they were each lyophilized. Each lyophilized sample was dissolved in 2.1 ml of 10 mM Tris.Cl (pH 7.2) and 100 mM NaCl. A 700 μl volume was loaded each time for filtration through a Hewlett Packer sample filter. A C8 column was used. The program for fractionation was as follows.

| Solvent A: Tris.Cl. 10 mM pH 7.2 | | | |
|---|---|---|---|
| Solvent B: Acetonitrile | | | |
| Time | % of A | % of B | Duration |
| 0' | 100 | 0 | |
| 5' | 50 | 50 | 50' |
| 55' | 50 | 50 | |
| 60' | 100 | 0 | 5' |
| 75' | | Stop | |

The C8 column was a 4.6×150 mm analytical column from Beckman.

After the C8 reverse phase chromatography, a second reverse phase chromatography was performed on a selected peak which had been lyophilized. The sample preparation, the loading volume, and the fractionation program were the same as for C8 reverse phase. However, this time a Beckman C3 column, 4.6×75 mm was used.

Both the test and control sera were totally run in three separate sets of loading. The final purified peaks were lyophilized for future biological activity testing. See FIGS. 1 to 5.

The serum from patients with renal insufficiency showed many peaks in the C8 chromatography profile. One peak eluted shortly after 22 minutes had a high 280 nm absorption relative to 214 nm absorption, somewhat similar to the active peak identified in the rat calcium deficient serum described in U.S. patent application Ser. No. 08/120,217 (now abandoned). This peak was put through a second C3 reverse phase chromatography and a single distinct peak appeared in the second run. This final peak material was kept for biological testing.

Compared with the test serum, the elution profile of the control serum was much simpler. No sample was taken for biological testing.

BIOLOGICAL ACTIVITY OF HUMAN ISOLATE IN RATS MATERIALS AND METHODS

The protein concentration of the test material was determined by the Belford method as described in U.S. patent application Ser. No. 08/120,217 (now abandoned). The lyophilized material was dissolved in 1.8 ml of Tris.Cl (pH 7.2) and 50 mM NaCl. An 80 µl volume was diluted to 800 µl with the same buffer and the protein concentration was measured in this diluted sample.

Twelve parathyroidectomized rats were used to test the effect of the isolate on the bone apposition rate in rats. Their pre-PTX and post PTX serum calcium concentration were 2.57 (S.D. 0.04) and 1.72 (S.D. 0.02) respectively. Six of the rats received the test material in 400 µl and six of the rats received 400 µl of carrier buffer as control. The bone mineral apposition rate was determined according to the same method as described in connection with material isolated from rat serum described in U.S. patent application Ser. No. 08/120,217 (now abandoned).

The concentration of the 10× diluted sample had a concentration of 3 µg/ml. Therefore the total amount of peptide was about 52 µg. 400 µl of the undiluted material contained about 12 µg of peptide. Therefore each test animal received 400 µl of the material intravenously. The bone mineral apposition rate was 1.89 µm/day (S.D. 0.13) and that of the control group was 0.72 µm/day (S.D. 0.08), this difference being statistically significant (P<0.025).

The results indicate that, at least in patients suffering from renal failure, there is an active peptide of low molecular weight capable of stimulating the bone mineral apposition rate in parathyroidectomized rats.

Early attempts at isolating and characterizing an active human peptide were not entirely successful. Amino acid sequencing of what was thought to be a peptide, isolated through the use of gel permeation chromatography and which was shown to increase bone apposition in rats, indicated that the peptide being sequenced was most likely serum albumin.

PROCEDURE FOR FRACTIONATION OF HUMAN SERUM PROTEIN AND POLYPEPTIDE FRACTIONS WITH MOLECULAR WEIGHTS BETWEEN 3K AND 30K BY TRICINE SDS GEL ELECTROPHORESIS

The millitan filtration system (Millipore) and MWCO membrane of 30K, was used to filter 500 ml of human serum (from BSC) at a pressure of between 7 and 12 psi. Filtration was stopped when the filtrate volume reached ⅔ of the original serum volume. The filtrate was then collected and concentrated down to 80 ml with the same type of filtration unit and MWCO membrane of 3K.

The pH of the concentrated filtrate was adjusted to about 8.8 by the addition of ammonium hydroxide. A 5 ml volume of Waters QMA anion exchange packing was packed into a mini disposable column and equilibrated with tris buffer at pH 8.8. The concentrated filtrate was passed through the column with a vacuum negative pressure. The filtrate was collected and its pH adjusted to 9.45 with the addition of ammonium hydroxide. Another QMA cartridge was packed and equilibrated with a weak ammonium hydroxide (10 mM) solution with the pH adjusted to 9.45 by the addition of acetic acid. The filtrate eluted from the first column was passed through this minicolumn. The filtrate was discarded. The column was washed with 15 ml of water the pH of which was adjusted to 10 with ammonium hydroxide. The material retained in the column was eluted with 3 ml of 0.1% acetic acid and lyophilized.

The lyophilized material was dissolved in 200 µl of loading buffer, and kept at 60° C. for 30 minutes prior to electrophoresis.

For electrophoresis, a 1 mm thick, (Novex) 10 well 10%–20% tricine gradient gel was used. A 20 µl volume of the sample was loaded into each well. The sample was co-run with the same volume of MW marker (Novex). Electrophoresis was carried out in a Novex gel apparatus at constant voltage of 100 V for 90 minutes. The gel was stained with Coomassie blue for 2 minutes in a microwave oven and for a further period of 20 minutes under gentle shaking. The gel was destained using 50% acid methanol for 1 hour and 10% acid methanol for 4 hours.

Details of the composition of the electrophoresis solutions are as follows:

| | | |
|---|---|---|
| TRICINE GEL MANUFACTURER: | NOVEX 4202 Sorrento Valley Boulevard San Diego, CA. 92121 | |
| GEL SIZE: | 8 × 8 cm | |
| GEL MATRIX: | Acrylamide/Bis-Acrylamide | |
| GEL THICKNESS: | 1.0 mm | |
| GEL TYPE: | 10–20% gradient | |
| SAMPLE BUFFER (2X) | To be diluted 1:1 with equal volume of sample in solution. | |
| | 3.0M Tris-HCL, pH 8.45 | 3.0 ml |
| | Glycerol | 2.4 ml |
| | SDS | 0.8 g |
| | 0.1% Coomassie Blue G | 1.5 ml |
| | 0.1% Phenol Red | 0.5 ml |
| | De-ionized water | to 10.0 ml |
| RUNNING BUFFER: | Tris Base | 121 g |
| | Tricine | 179 g |
| | SDS | 10 g |
| | De-ionized water | to 1 L |
| SAMPLE LOADING VOLUME: | 20 µl | |
| RUNNING CONDITION: | Constant voltage at 100 V | |
| GEL APPARATUS: | NOVEX | |
| POWER SUPPLY: | NOVEX | |
| STAINING OF GEL: | | |
| STAINING SOLUTION: | Coomassie Blue R-250 | 0.5 g |
| | Methanol | 800 ml |
| | Acetic acid | 140 ml |
| | De-ionized water | to 2 L |
| DESTAINING SOLUTIONS: | | |
| SOLUTION I. | | |
| (50% ACID METHANOL) | Methanol | 500 ml |
| | Acetic acid | 100 ml |
| | De-ionized water | to 1 L |
| SOLUTION II. | | |
| (10% ACID METHANOL) | Methanol | 100 ml |
| | Acetic acid | 70 ml |
| | De-ionized water to | 1 L |

Figure 6:
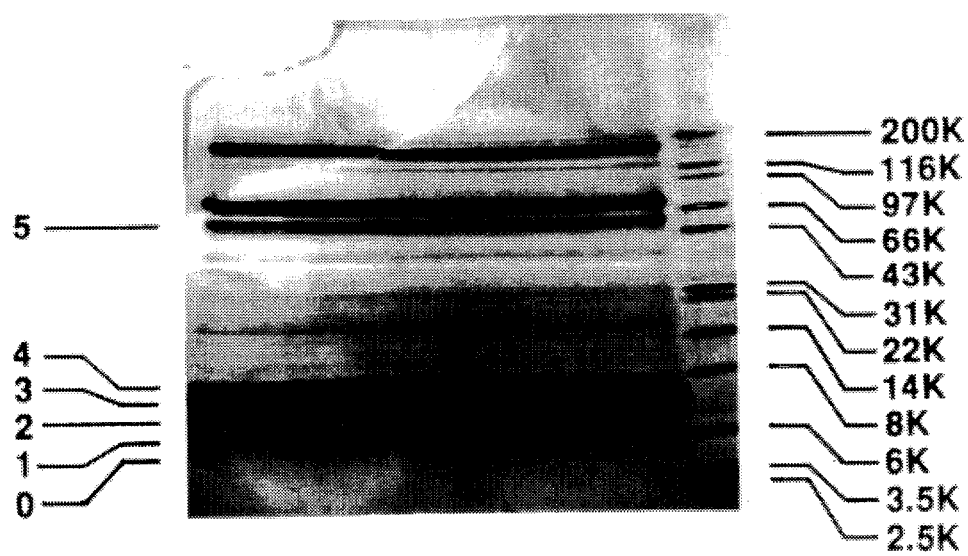
FIG. 6 shows a tricine SDS electrophoretic gel of human serum protein and polypeptide fractions of material collected at pH 9.45 on a minicolumn packed with Waters QMA anion exchange packing.

A photograph of the electrophoretic gel obtained from the isolate from about 1000 ml of human serum using the foregoing procedure is shown in FIG. 6. As can be seen, four major bands lie in the molecular weight range of 4 to 12K in the Tricine SDS electrophoretic gel.

WESTERN TRANSFER FROM SDS GEL TO PVDF MEMBRANE

A PVDF membrane (Novex) was soaked in 100% methanol for fifteen minutes, rinsed with transfer buffer, and soaked in the buffer for another fifteen minutes before use.

The destained gel was rinsed two times in the transfer buffer and then soaked in the buffer for about fifteen minutes. The cathode of a Novex gel transfer unit was wetted with the buffer and one mesh placed on the cathode. One filter paper was laid on the mesh and the gel onto the filter paper. The pre-soaked PVDF membrane was placed on the gel and another piece of filter paper placed on the membrane. Three layers of mesh were placed on the second filter paper and the anode (pre-wetted in buffer) onto the top mesh. The cathode and anode of the unit were pressed together and installed into the transfer housing and the unit was then filled with transfer buffer. The housing was filled with water and electrodes connected to the power supply. The transfer was carried out at a constant voltage of 30 V for 1½ hours.

After transfer, the membrane was washed with deionized water and dried on a sheet of chromatography paper.

The transfer buffer used in the above steps had the following composition: 12 mM Tris and 96 mM glycine in 20% methanol at pH 8.3.

ISOLATION OF BANDS FROM PVDF MEMBRANE

Bands labelled 0, 1, 2, 3 and 5 in FIG. 6 were cut from the membrane. An additional band having a molecular weight above the molecular weight range of these bands was cut from the membrane for use as a control.

The polypeptides were separately eluted from the bands using the following procedure. A band was soaked in 3 ml of 70% isopropanol and 0.1% TFA overnight at 37° C. The soaking solution was collected and another was added and the band soaked for another two hours at 37° C. The two 3 ml solutions were pooled and evaporated down to about 1 ml in a Speed Vac. The resulting sample was then dialysed against 0.1% acetic acid in a micro-dialyser (Amicon 8MC) to remove dye and SDS. The sample volume was raised to 2 ml with 0.1% acetic acid.

MODIFIED PROCEDURE FOR FACTIONATION OF HUMAN SERUM PROTEIN AND POLYPEPTIDE FRACTIONS WITH MOLECULAR WEIGHTS BETWEEN 3K AND 30K BY TRICINE SDS GEL ELECTROPHORESIS

A 1000 ml volume of human serum was filtered as described above, and concentrated down to 100 ml.

The pH of the concentrated filtrate was adjusted to about 8.8 with TEAA buffer. 5 g of Millipore Acell™ QMA packing was equilibrated with 25 mM TEAA (pH 8.8). The packing was added to the serum extract and stirred for 15 minutes. The packing was filtered off and the filtrate collected. Another 5 g of the same packing was equilibrated with 25 mM TEAA (pH 9.45) and then added to the filtrate and stirred for 15 minutes. The packing was then transferred to a disposable minicolumn (15 ml capacity) and washed with a weak ammonia solution (pH 10.2). Polypeptides adsorbed to the packing were eluted with 8 ml of 0.1% acetic acid and the sample lyophilized.

The lyophilized material was dissolved in 200 µl of loading buffer and treated as described above. Electrophoresis was carried out on a 25 µl volume of sample as described above for two hours.

Figure 7:
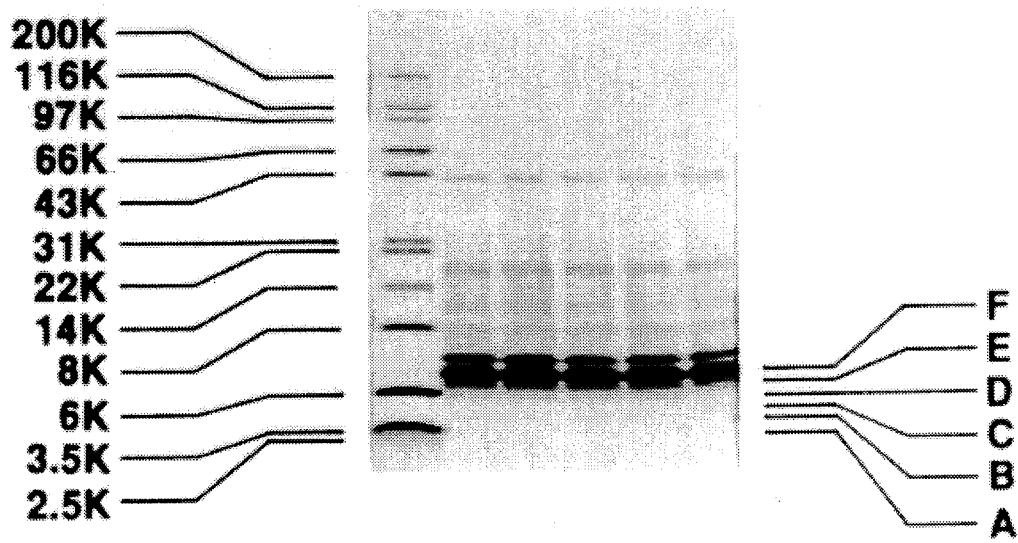
FIG. 7 shows a tricine SDS electrophorectic gel of human serum protein and polypeptide fractions of material collected at pH 9.45 according to an modified procedure.

A photograph of the electrophoretic gel obtained from the isolate from about 1000 ml of human serum using the foregoing procedure is shown in FIG. 7. Six bands, labelled A to F in FIG. 7, within the molecular weight range of 4 to 10K were cut out and ground up and soaked in 3 ml of 50 mM NH$_4$HCO$_3$ and 0.1% SDS for 12 hours at 37° C. The supernatant was collected and another 3 ml of the same buffer was added to the gel and soaked for another 6 hours. The supernatant was pooled and dialysed against 0.1% acetic acid with a MWCO membrane of 1K, using the Amicon 8MC microdialyzer. The final volume of the dialysed sample was adjusted to 4 ml with 0.1% acetic acid.

BIOLOGICAL TESTING FOR ACTIVITY OF POLYPEPTIDES ISOLATED ACCORDING TO MODIFIED FRACTIONATION PROCEDURE

Figure 8:
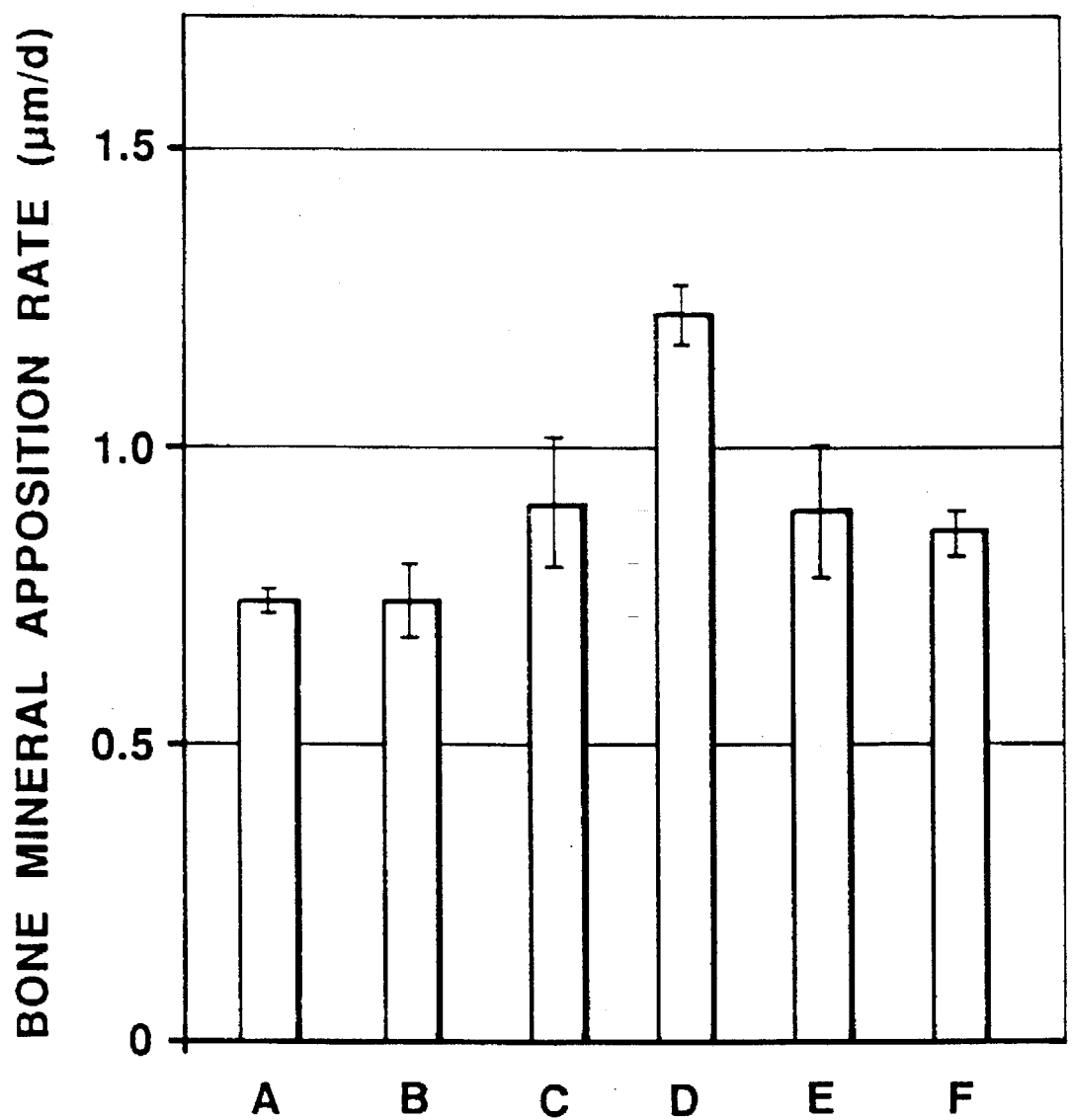
FIG. 8 shows the bone apposition rate (μm per day) for rats injected with material from bands bands A (N=4), B (N=4), C (N=4), D (N=3), E (N=4) and F (N=4) obtained through the modified fractionation procedure and SDS gel electrophoresis. The error bars are ±1 S.D.

The bone apposition rate was measured over a period of 48 hours as described above on six groups of rats using 1 ml of the eluted peptide. Each solution was injected intramuscularly into a group of animals followed by tetracycline at 24 mg per kg of bodyweight. Sections of the lower femoral metaphysis were used for bone apposition measurements. The results are presented in Table One and shown graphically in FIG. 8.

TABLE ONE

Comparison of the Group Arithmetic Means of Bone Apposition Rates (µm/day) Among Groups (Bands A, B, C, D, E and F of FIG. 7)

| BAND | A | B | C | D | E | F |
|------|------|------|------|------|------|------|
| MEAN | 0.85 | 0.85 | 0.91 | 1.23 | 0.90 | 0.87 |
| S.D. | 0.02 | 0.06 | 0.11 | 0.05 | 0.11 | 0.04 |
| N    | 4    | 4    | 4    | 3    | 4    | 4    |

SEQUENCING OF MATERIAL ISOLATED FROM PVDF MEMBRANE

The material of Band 2 shown in FIG. 6, which corresponds to Band D of FIG. 7 was sequenced according to standard procedures. The sequence of the first eighteen N-terminal amino acids were found to be: Asp Ser Asp Leu Tyr Ala Glu Leu Arg Xaa Met Xaa Ile Lys Thr Thr Ser Gly (SEQ ID NO:6), this sequence approximately corrresponding with the first nineteen amino acids given for a variant of NAP-2, described by Walz et al. (27), identified herein as SEQ ID NO:4 or NAP-2V.

An analysis of total amino acid content of the polypeptide isolated from human serum also gave good agreement with the amino acid content of NAP-2V. Correspondence of all acid residues measured (i.e., all residues except asparagine, cysteine and glutamine) was within one or two of the expected content except for leucine, isoleucine and lysine. This is a common observation for leucine and isoleucine, but not for lysine.

It will of course be understood, without the intention of being limited thereby, that a variety of substitutions of amino acids is possible while "preserving" the three-dimensional structure responsible for the bone stimulatory effect of the polypeptide disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, cysteine, asparagine and glutamine could possibly be made. This being said, the linkage of the peptides together by the disulfide bridge might be of importance, and if so the lone cysteine residue should probably be held intact and other amino acids capable of forming a disulfide linkage not be substituted elsewhere in the sequence. Substitutions among the charged acidic amino acids, aspartic acid and glutamic acid, could probably be made, as could substitutions among the charged basic amino acids, lysine and arginine. Substitutions among the aromatic amino acids, including phenyalanine, histidine, tryptophan and tyrosine would also likely be possible. These sorts of substitutions and interchanges are well known to those skilled in the art. Other substitutions might well be possible. It is thought that a peptide having an amino acid sequence with about 50% homology or more with the sequence identified as SEQ ID NO:4 may well retain part or all of the bone stimulating activity of the NAP-2V sequence. In the context of this invention, a peptide containing an amino acid sequence that can be aligned with that of SEQ ID NO:4 such that at least about 50% of individual amino acid residues of the NAP-2V sequence are conserved, allowing for a limited number of insertions or deletions between aligned sequences, would meet this criterion. Of course, it would also be expected that the greater percentage of homology, say 60%, 70%, 80%, 90%, or more, could increase the degree of retained bone stimulating activity.

Insofar as deletion of one or more amino acids is concerned, it is likely that deletions of a small number of amino acids from each end of the sequence might be possible. Further, symmetrical, or nearly symmetrical deletions would likely be the most possible to be made while retaining the three-dimensional configuration. Internal deletions, although likely to be possible to some limited extent, should be few, and should probably amount to no more than about five amino acids.

Additions of amino acids could very likely be made at the ends of the sequence, and as with deletions, symmetrical or nearly symmetrical additions to the carboxy and amino terminals are likely to be possible. Internal additions, although likely to be possible to some limited extent, should be few, and should probably amount to no more than about five amino acids, and preferrably fewer.

Of the above-listed modifications to the sequence, terminal additions, deletions or substitutions are most likely to be most useful, as such a modification can serve a variety of functions: an identifying group as for use in a radioimmunoassay; or a linking group, as examples.

The polypeptide made available by the invention disclosed herein can thus be used to obtain antisera thereto (28). Methodology and products can be developed using an antibody to a polypeptide for use in detecting the polypeptide with which the antibody binds.

For example, an antibody can be linked to or conjugated with a reporter system which is set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluroescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such a method based on antigenic response to NAP-2V (SEQ ID NO:4) could be developed. Variants of the polypeptide obtained, as described above for amino acid subsitution, deletion and addition, (and conjugates) could then be pre-screened as potential bone stimulating factors. Those that react positively with the antibody to the already known peptide could then be tested for bone stimulatory effects in vivo using the system described herein for rats, for example.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

A further advantage may be obtained through chimeric forms of the protein, as known in the art. A DNA sequence encoding the entire protein, or a portion of the protein, could thus be linked with a sequence coding for the C-terminal portion of *E. coli* β-galactosidase to produce a fusion protein, for example. An expression system for human respiratory syncytial virus glycoproteins F and G is described in U.S. Pat. No. 5,288,630, issued Feb. 22, 1994, and references cited therein, for example.

REFERENCES

1. Tam, C. S. 1989. The Pathogenesis of Metabolic Bone Disease: An Overview. In Metabolic Bone Disease: Cellular and Tissue Mechanisms. Eds. Tam, C. S., Heersche, J. N. M and Murray, T. M. CRC Press, Boca Raton.

2. Parfitt A. M., Villanueva, A. R., Mathews, C. H. E., Aswani, S. A. 1980. Kinetics of matrix and mineral apposition in osteoporosis and renal osteodystrophy: relation of rate of turnover to cell morphology, Metab Bone Dis Rel Res, 2(S), 213.

3. Parfitt A. M. 1982. The coupling of bone formation to bone resorption: A critical analysis of the concept and of its relevance to the pathogenesis of osteoporosis. Metab Bone Dis Rel Res 4, 1.

4. Coccia, P. F., Krivit, W. Cerveuka, J., Clawson, C., Kersey, J., Kim, T. H., Nesbit, M. E., Ramsey, N. K. C., Warkeutin, P. I., Teitelbaum, S. L., Kahn, A. J., Brown, D. M. 1980. Successful bone marrow transplantation for infantile malignant osteopetrosis. New Eng J. Med, 302, 701.

5. Marks, S. C. Jr., Walker, D. G. 1981. The hematogenous origin of osteoclast: evidence form osteopetrotic (microphthalamic) mice treated with spleen cell from geige mouse donor. Am J Anal 161,1.

6. Owen M. 1985. Lineage of osteogenic cells and their relationship to the stromal system. In Bone and Mineral Research, Vol 3, Ed. Peck W. A. Amsterdam 1.

7. Yamamoto, I. 1985. Regulation of receptors for parathyroid hormone in rat osteosarcoma cells. J. J. B. M. 3,38.

8. Canalis, E. 1986. Interleukin-1 has independent effects on deoxyribonucleic acid and collagen synthesis in cultures of rat calvariae, Endocrinol 118, 74.

9. Centrella, M., Canalis, E. 1985. Transforming and non-transforming growth factor are present in medium conditioned by fetal rat calvariae. Proc Natl Acad Sci, U.S.A. 82, 7355.

10. Canalis, E. 1985. Effect of growth factors on bone cell replication and differentiation. Clin Orthop 183, 246.

11. Chyun, Y. S., Raisz, L. G. 1984. Stimulation of bone formation by prostaglandin E2. Prostaglandins, 27, 97.

12. Canalis, E. 1980. Effects of insulin-like growth factor 1 on DNA and protein synthesis in cultured rat calvariae. J Clin Invest, 66, 709.

13. Klein, D. C., Raisz, L. G. 1970. Prostaglandins: stimulation of bone resorption in tissue culture. Endocrinol 86 1436.

14. Tashjian A. H., Jr., Voekel, E. F., Lazarro, M., Singer, F. R., Roberts, A., Derynck, R., Winkler, M. E., Levine, L. 11985. a and b human transforming growth factors stimulate protaglandin production and bone resorption in cultured mouse calvariae. Proc Natl Acad Sci, U.S.A. 82, 4535.

15. Chen, T. L., Cone, C. M., Morey-Holton, E., Feldman, D. 1982. Glucocorticoid regulation of 1,25(OH)$_2$D3 receptors on cultured mouse bone cells. J. Biol Chem 257, 13563.

16. Roodman, G. D. 1992. Perspectives: Interleukin-6: An osteotropic factor. J. Bone Miner Res, 7, 475.

17. Segre G. V. 1990 Secretion, metabolism and circulating heterogeneity of parathyroid hormone. In Primer in Metabolic Bone diseases and Disorders of Mineral Metabolism. First Edition. ed. Favus, M. J,. Kelseyville, Calif.

18. Selye H. 1933. On the stimulation of new bone formation with parathyroid extract and irradiated ergosterol. Endocrinol 16, 547.

19. Aitken R. E., Kerr J. L., Loyd H. M. 1964. Primary hyperparathyroidism with osteosclerosis and calcification in articular cartilage. Am J Med 37, 813.

20. Connor T. B., Freijances J., Stoner R. E., Martin L. G., Jowsey J. 1973. Generalized osteosclerosis in primary hyperparathyroidism. Trans Am Clin Climatol Assoc 85, 185.

21. Gennant H. K., Baron J. M., Paloyan E., Jowsey J. 1975. Osteosclerosis in primary hyperparathyroidism. Am J Med 59, 104.

22. Kalu, D. N., Pennock J., Doyle, F. H., Foster G. V. 1970. Parathyroid hormone and experimental osteosclerosis. Lancet 1, 1363.

23. Tam C. S., Harrison J. E., Reed R., Cruickshank B. 1978. Bone apposition rate as an index of bone metabolism. Metabolism 27, 143.

24. Tam C. S., Bayley T. A., Harrison J. E., Murray T. M., Birkin B. L., Thompson D. 1978. Bone biopsy in the diagnosis of primary hyperparathyroidism. In Copp D. H., Talmage R. V. (eds) Endocrinology of Calcium Metabolism. Excerpta Medica, Amsterdam, p 427 (Abstract).

25. Tam, C. S., Heersche, J. N. M., Murray, T. M., Parsons J. A. 1982. Parathyroid hormone stimulates the apposition rate independent of its resorptive action: Differential effects of intermittent and continuous administration. Endocrinol 110, 506.

26. Majundar, S., Gonder, D., Koutsis, B., Poncz, M. 1991. Characterization of Human β-Thromboglobulin Gene. J. Biol Chem 266, 5785.

27. Walz, A., Baggiolini, M. 1990. Generation of the Neutrophil-Activating Peptide NAP-2 from Platelet Basic Protein or Connective Tissue-Activating Peptide III Through Monocyte Proteases. J. Exp Med 171, 449.

28. Basic & Clinical Immunology, (7th Edition) eds. Stites, Daniel P., Terr, Abba I, Appleton and Lange, Norwalk, Connecticut, San Matea, Calif., 1991.

---

|-----|-----|

What is claimed is:

1. A method of increasing bone growth in a mammal by administering a therapeutically effective amount of a polypeptide having the amino acid sequence of SEQ ID NO: 4: $NH_2$-Asp-Ser-Asp-Leu-Tyr-Ala-Glu-Leu-Arg-Cys-Met-Cys-Ile-Lys-Thr-Thr-Ser-Gly-Ile-His-Pro-Lys-Asn-Ile-Gln-Ser-Leu-Glu-Val-Ile-Gly-Lys-Gly-Thr-His-Cys-Asn-Gln-Val-Glu-Val-Ile-Ala-Thr-Leu-Lys-Asp-Gly-Arg-Lys-Ile-Cys-Leu-Asp-Pro-Asp-Ala-Pro-Arg-Ile-Lys-Lys-Ile-Val-Gln-Lys-Lys-Leu-Ala-Gly-Asp-Glu-Ser-Ala-Asp-$CO_2H$, or a conservatively substituted variant thereof.

2. A method of increasing bone growth as claimed in claim 1, wherein the polypeptide has at least about 50% homology with SEQ ID NO:4.

3. The method of increasing bone growth in a mammal according to claim 2 wherein the amino sequence has at least about 60% homology with SEQ ID NO:4.

4. The method of increasing bone growth in a mammal according to claim 3 wherein the amino sequence has at least about 70% homology with SEQ ID NO:4.

5. The method of increasing bone growth in a mammal according to claim 4 wherein the amino sequence has at least about 80% homology with SEQ ID NO:4.

6. The method of increasing bone growth in a mammal according to claim 5 wherein the amino sequence has at least about 90% homology with SEQ ID NO:4.

7. The method as claimed in claim 1, wherein the polypeptide is SEQ ID NO: 4.

8. The method as claimed in claim 1, wherein at least one non-polar aliphatic neutral amino acid of SEQ ID NO: 4 is substituted by a different non-polar aliphatic neutral amino acid.

9. The method as claimed in claim 1, wherein at least one polar aliphatic neutral amino acid of SEQ ID NO: 4 is substituted by a different polar aliphatic neutral amino acid.

10. The method as claimed in claim 1, wherein at least one charged acidic amino acid of SEQ ID NO: 4 is substituted by a different charged acidic amino acid.

11. The method as claimed in claim 1, wherein at least one charged basic amino acid of SEQ ID NO: 4 is substituted by a different charged basic amino acid.

12. The method as claimed in claim 1, wherein at least one aromatic amino acid of SEQ ID NO: 4 is substituted by a different aromatic amino acid.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 81 amino aicds
    ( B ) TYPE: amino acid
    ( D ) TOPOLOGY: linear ( x i ) SEQUENCE DESCRIPTION: SEQ ID NO:1:

```
Gly Lys Glu Glu Ser Leu Asp Ser Asp Leu Tyr Ala Glu Leu Arg Cys
 1           5                   10                  15
Met Cys Ile Lys Thr Thr Ser Gly Ile His Pro Lys Asn Ile Gln Ser
            20                  25                  30
Leu Glu Val Ile Gly Lys Gly Thr His Cys Asn Gln Val Glu Val Ile
            35                  40                  45
Ala Thr Leu Lys Asp Gly Arg Lys Ile Cys Leu Asp Pro Asp Ala Pro
        50                  55                  60
Arg Ile Lys Lys Ile Val Gln Lys Lys Leu Ala Gly Asp Glu Ser Ala
65                  70                  75                  80
Asp
```

( 2 ) INFORMATION FOR SEQ ID NO:2:

( i ) SEQUENCE CHARACTERISTICS:
    ( A ) LENGTH: 70 amino acids
    ( B ) TYPE: amino acid ( D ) TOPOLOGY: linear ( x i ) SEQUENCE DESCRIPTION: SEQ ID NO:2:

| Ala | Glu | Leu | Arg | Cys | Met | Cys | Ile | Lys | Thr | Thr | Ser | Gly | Ile | His | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Lys | Asn | Ile | Gln | Ser | Leu | Glu | Val | Ile | Gly | Lys | Gly | Thr | His | Cys | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Val | Glu | Val | Ile | Ala | Thr | Leu | Lys | Asp | Gly | Arg | Lys | Ile | Cys | Leu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Asp | Pro | Asp | Ala | Pro | Arg | Ile | Lys | Lys | Ile | Val | Gln | Lys | Lys | Leu | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Asp | Glu | Ser | Ala | Asp |
|-----|-----|-----|-----|-----|-----|
| 65  |     |     |     |     | 70  |

( 2 ) INFORMATION FOR SEQ ID NO:3:

( i ) SEQUENCE CHARACTERISTICS:
( A ) LENGTH: 85 amino acids
( B ) TYPE: amino acid
( D ) TOPOLOGY: linear ( x i ) SEQUENCE DESCRIPTION: SEQ ID NO:3:

| Asn | Leu | Ala | Lys | Gly | Lys | Glu | Glu | Ser | Leu | Asp | Ser | Asp | Leu | Tyr | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Leu | Arg | Cys | Met | Cys | Ile | Lys | Thr | Thr | Ser | Gly | Ile | His | Pro | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asn | Ile | Gln | Ser | Leu | Glu | Val | Ile | Gly | Lys | Gly | Thr | His | Cys | Asn | Gln |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Val | Glu | Val | Ile | Ala | Thr | Leu | Lys | Asp | Gly | Arg | Lys | Ile | Cys | Leu | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Pro | Asp | Ala | Pro | Arg | Ile | Lys | Lys | Ile | Val | Gln | Lys | Lys | Leu | Ala | Gly |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asp | Glu | Ser | Ala | Asp |
|-----|-----|-----|-----|-----|
|     |     |     |     | 85  |

( 2 ) INFORMATION FOR SEQ ID NO:4:

( i ) SEQUENCE CHARACTERISTICS:
( A ) LENGTH: 75 amino acids
( B ) TYPE: amino acid
( D ) TOPOLOGY: linear ( x i ) SEQUENCE DESCRIPTION: SEQ ID NO:4:

| Asp | Ser | Asp | Leu | Tyr | Ala | Glu | Leu | Arg | Cys | Met | Cys | Ile | Lys | Thr | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Gly | Ile | His | Pro | Lys | Asn | Ile | Gln | Ser | Leu | Glu | Val | Ile | Gly | Lys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Thr | His | Cys | Asn | Gln | Val | Glu | Val | Ile | Ala | Thr | Leu | Lys | Asp | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Arg | Lys | Ile | Cys | Leu | Asp | Pro | Asp | Ala | Pro | Arg | Ile | Lys | Lys | Ile | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gln | Lys | Lys | Leu | Ala | Gly | Asp | Glu | Ser | Ala | Asp |
|-----|-----|-----|-----|-----|-----|-----|-----|-----|-----|-----|
| 65  |     |     |     |     | 70  |     |     |     |     | 75  |

( 2 ) INFORMATION FOR SEQ ID NO:5:

( i ) SEQUENCE CHARACTERISTICS:
( A ) LENGTH: 36 amino acids
( B ) TYPE: amino acid
( D ) TOPOLOGY: linear (xi) SEQUENCE DESCRIPTION: SEQ ID NO:5:

| Gly | Ile | Gly | Lys | Arg | Thr | Asn | Glu | His | Thr | Ala | Asp | Cys | Lys | Ile | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Asn | Thr | Leu | His | Lys | Lys | Ala | Ala | Glu | Thr | Leu | Met | Val | Leu | Asp |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Asn | Gln | Pro |
|-----|-----|-----|-----|
|     |     | 35  |     |

(2) INFORMATION FOR SEQ ID NO:6:

(i) SEQUENCE CHARACTERISTICS:
      (A) LENGTH: 18 amino acids
      (B) TYPE: amino acid
      (D) TOPOLOGY: linear (xi) SEQUENCE DESCRIPTION: SEQ ID NO:6:

| Asp | Ser | Asp | Leu | Tyr | Ala | Glu | Leu | Arg | Xaa | Met | Xaa | Ile | Lys | Thr | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Gly |